United States Patent
Blackmore et al.

(10) Patent No.: US 7,671,345 B2
(45) Date of Patent: Mar. 2, 2010

(54) METHOD OF ANALYSING A SAMPLE AND APPARATUS THEREFOR

(75) Inventors: Colin Blackmore, Welwyn Garden (GB); Patrick Courtney, Ealing (GB); Alistair Fitch, Maidenhead (GB); Shab Ladha, Chalfont St. Giles (GB)

(73) Assignee: PerkinElmer Singapore PTE Ltd., Singapore (SG)

( * ) Notice: Subject to any disclaimer, the term of this patent is extended or adjusted under 35 U.S.C. 154(b) by 233 days.

(21) Appl. No.: 11/658,829

(22) PCT Filed: Aug. 17, 2005

(86) PCT No.: PCT/GB2005/003226

§ 371 (c)(1),
(2), (4) Date: Jan. 26, 2007

(87) PCT Pub. No.: WO2006/024819

PCT Pub. Date: Mar. 9, 2006

(65) Prior Publication Data

US 2008/0315119 A1    Dec. 25, 2008

(30) Foreign Application Priority Data

Sep. 1, 2004 (GB) .................. 0419325.6
Jun. 23, 2005 (GB) .................. 0512811.1

(51) Int. Cl.
  *G01J 1/58* (2006.01)
(52) U.S. Cl. .................. 250/459.1; 250/458.1
(58) Field of Classification Search .............. 250/458.1, 250/459.1, 462.1
See application file for complete search history.

(56) References Cited

U.S. PATENT DOCUMENTS 6,466,316 B2 * 10/2002 Modlin et al. ............... 356/318
2003/0026762 A1 * 2/2003 Malmros et al. ............ 424/9.6

FOREIGN PATENT DOCUMENTS

EP         1146480 A1 * 10/2001

OTHER PUBLICATIONS

Sabanayagam et al., "High-throughput scanning confocal microscope", Applied Physics Letters, vol. 84, Nr. 7, Feb. 16, 2004, pp. 1216-1218.*
Benson et al., "Digital Imaging Fluorescence Microscopy: Spatial Heterogeneity of Photobleaching Rate Constants in Individual Cells", The Journal of Cell Biology, vol. 100, Apr. 1, 1985, pp. 1309-1323.*
Chudakov et al., "Kindling fluorescent proteins for precise in vivo photolabeling", Nature Biotechnology, vol. 21, Jan. 13, 2003, pp. 191-194.*
Paterson et al., "Photoporation and cell transfection using a violet diode laser", Optics Express, vol. 13, Nr. 2, Jan. 24, 2005, pp. 595-600.*

* cited by examiner

*Primary Examiner*—David P Porta
*Assistant Examiner*—Mark R Gaworecki
(74) *Attorney, Agent, or Firm*—Barnes & Thornburg LLP (57) ABSTRACT

A method for performing photo-modification of a biological sample, the method comprising: (a) irradiating the sample; (b) detecting one or more signals based on the irradiated sample; (c) using one or more processor means to analyze the detected signals and determine one or more irradiation parameters, and, (d) returning to (a) conditioned on the irradiation parameters. Thus modifications may be determined and executed interactively as an experiment progresses, and therefore directed towards specific structures and/or events identified as of particular interest in the course of the experiment.

14 Claims, 11 Drawing Sheets

METHOD OF ANALYSING A SAMPLE AND APPARATUS THEREFOR

FIELD OF THE INVENTION

This invention relates to a method and apparatus for analysing samples of biological material. More particularly, it concerns the investigation of processes in samples such as cells, in a way that may not interfere with cell functioning. Such investigation may provide greater understanding of complex processes in life science and medicine, assist the evaluation of new drug candidates, and enable the detection of disease or abnormal processes.

BACKGROUND

Examination of live samples provides access to the dynamics of cellular and sub-cellular processes. The study of small-scale cellular processes has typically been carried out using light microscopy.

In some cases, the complexity of the processes is such that tools are required to isolate specific types of processes which can be studied in isolation, or in combination with a small number of other processes. The use of labels (in the form of fluorescent molecules in fluorescence microscopy) has provided tools of this nature.

A label may be extrinsic (that is, added to a sample) or intrinsic (such as a molecule which is present in the sample that is inherently distinctively coloured or fluorescent).

A fluorescent molecule has a specific excitation spectrum, being more strongly excited at some wavelengths and less strongly excited at others. It also has a specific emission spectrum, emitting more intensely at some wavelengths, and less intensely at others. The excitation and emission spectra may range from the ultraviolet to the infrared.

A wide range of fluorescent labels have been developed from chemical molecules, such as Rhodamine and Fluoroscein. Further fluorescent labels have been developed from molecules found in luminescent organisms, for example the *Aequorea* Jellyfish which has provided the Green Fluorescent Protein (GFP), and various corals providing DsRed and HcRed. These have been termed AFPs (Aequorea Fluorescent Proteins).

The fluorescent labels may be associated with specific molecules of interest (DNA, RNA, proteins, carbohydrates, antibodies, etc). Alternatively they may be made to be sensitive to certain characteristics (such as ionic concentration, pH, voltage potential, temperature, the presence of a specific enzyme, the presence of specific enzyme substrates, force), altering their fluorescent properties according to these characteristics. These labels may be introduced into cells by passing through the cell membrane or by injection. Alternatively they may be formed internally as part of the normal functioning of the cell, in the case of the genetically encoded labels such as the AFPs.

Figure 1A:
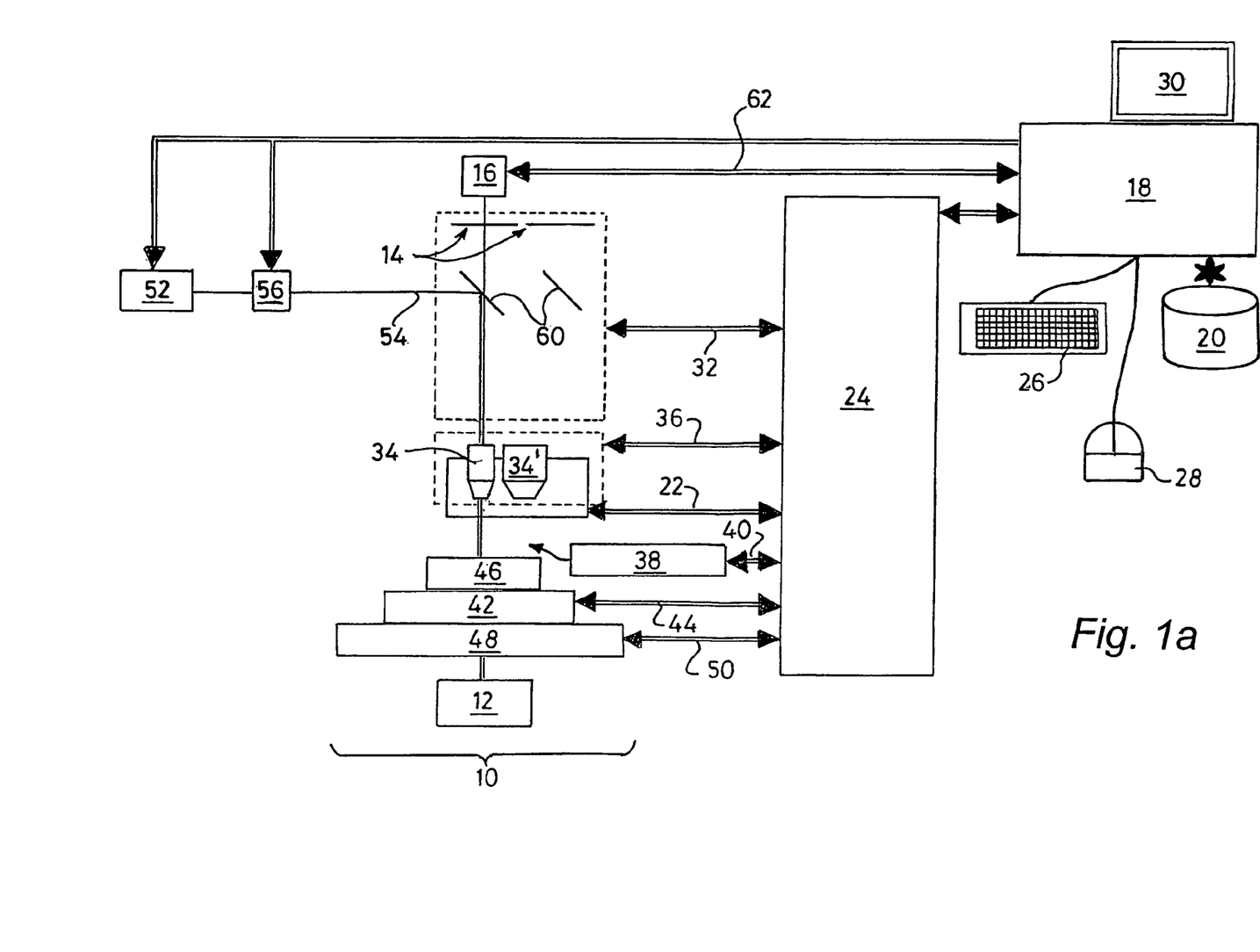
FIG. 1a shows a block diagram of a known light microscopy apparatus for investigating processes in a sample.

In a known apparatus for imaging samples as shown in FIG. 1a, a microscope 10 is fitted with a light source 12 for illuminating a sample 4b. It may be in the form of a lamp, laser or light emitting diode, for example. The microscope is fitted with optical filters 14 so that the light emanating from the sample may be observed at selected wavebands. Examination of the spatial and temporal distribution of light from the sample may provide information on the structure and dynamics of the sample.

Phase contrast illumination may be employed to enhance imaging of thin samples. Polarised light may be used to permit the visualisation of very thin samples with small refractive index changes, for example using differential interference contrast (DIC) techniques.

The microscope is fitted with an image acquisition system, comprising a light sensitive detector 16 (sensitive from the ultraviolet to the infrared) such as a CCD camera, and recording means such as a video recorder or computer 18 with a memory device 20, so that dynamic behaviour of the sample may be captured and analysed offline. For example, the velocity, distance traveled and path of moving parts of the sample may be monitored.

The system may employ a focus drive mechanism for altering the position of the imaging focus plane. Various algorithms may be used to establish and maintain the optical focal plane. Volumetric (XYZ) and volumetric time series (XYZT) data may be acquired using deconvolution techniques. By selecting suitable excitation wavebands and/or selecting suitable optical filter sets, volumetric multi-wavelength (XYWZ) and volumetric multi-wavelength time series (XYWZT) data may be acquired.

Operations of the microscope are controlled by a microscope controller 24 in response to commands from processing means in the form of computer 18. Instructions may be entered into the computer by a user using keyboard 26, a mouse 28 and a display 30.

By way of example, FIG. 1a shows control lines extending from the controller to the microscope for aspects such as filter selection along line 32, selection of an objective lens 34, 34' along line 36, focus along line 22, a liquid dispenser 38 along line 40, an environmental unit 42 along line 44 for modifying environmental conditions of a sample 46, and a sample transport unit 48 for moving the sample 46 relative to a lens of the microscope by control via line 50.

The apparatus may also include an activation light source 52 for generating an activating light beam 54 for use as discussed below. The direction of the activating light beam may be adjusted by a guide 56.

The activating light beam 54 is incident on a dichroic mirror 60. The mirror directs the beam towards an objective lens 34, and the beam is then incident on the sample 46. Light emanating from the sample 46 passes back through the objective lens 34, but is not diverted by mirror 60 so that is passes through a filter 14 before impinging on detector 16. An output signal from the detector 16 is fed to the computer 18 along line 62.

The environmental unit 42 may control the temperature of the sample, and/or the composition and flow of gas over the sample, for example.

Software loaded onto the computer enables it to acquire image data carried on the output signal from the detector.

The software also allows the user to select parameters for the operation of various aspects of the apparatus, such as the activating light beam, for example.

The controller allows the activating light beam to be directed by the setting of one or more of the following parameters:

- the one or more regions of interest on the sample (location, size and shape)
- the wavebands
- the power level
- the time of start of activation
- the duration of activation
- the number of repeat activation cycles
- the delay between activation cycles.

The computer permits recording of the image data from the detector via a digitiser at a given data rate. The filter sets in the microscope and the waveband of the illuminating light source 12 may be controlled to permit acquisition of data sets of one or more wavelengths.

Figure 1B:
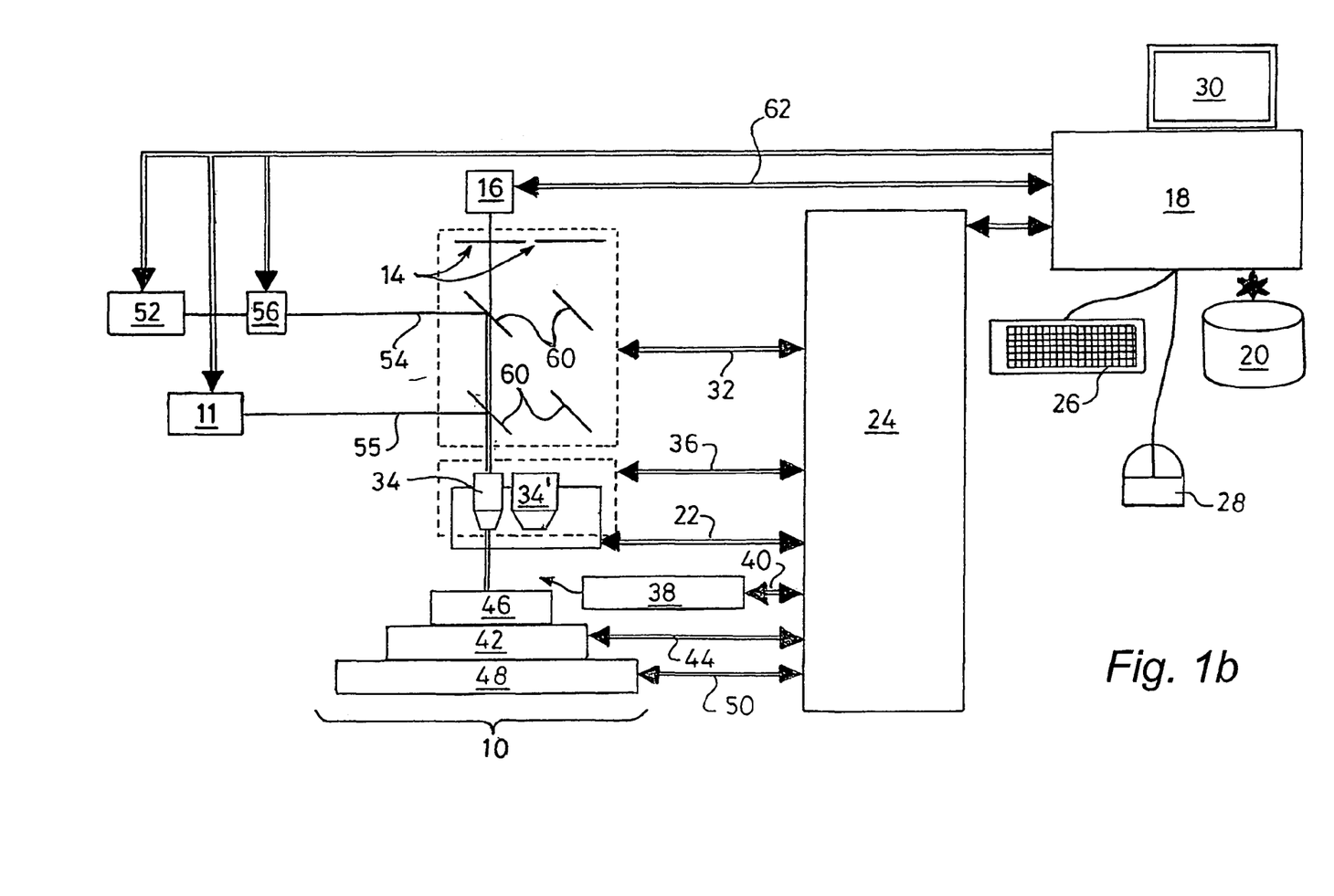
FIG. 1b shows a block diagram of a known fluorescence microscopy apparatus for investigating processes in a sample.

A known apparatus for imaging biological samples including fluorescent labels is shown in FIG. 1b. It is similar to the apparatus shown in FIG. 1a. However, instead of illumination light source 12, it includes an excitation light source 11, which generates a light beam 55. This light source is capable of exciting one or more fluorescent labels present in the sample by irradiating them with one or more specific wavebands. Filters 14 may be chosen so as to pass light emitted by labels at selected wavebands.

Figure 1C:
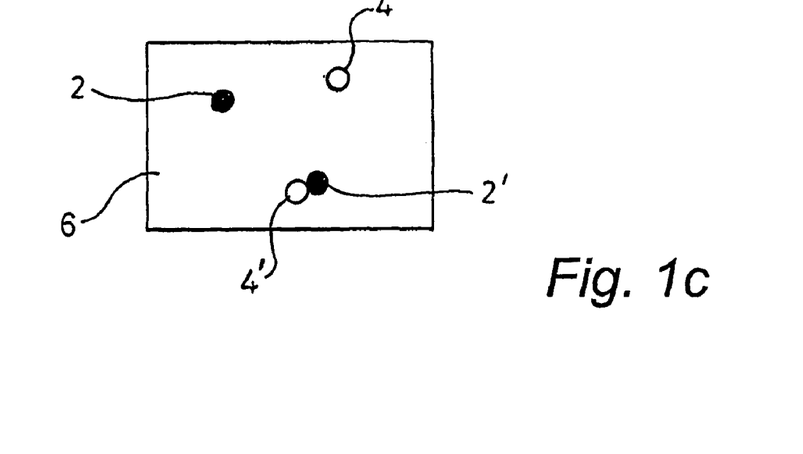
FIG. 1c illustrates known use of fluorescent labels.

FIG. 1c illustrates attachment of a fluorescent label 2, 2' to a component of interest 4, 4' in a sample 6. Multiple labels may be used to provide information on the coincident localisation of labelled components, revealing, for example, the organization of the cytoskeleton of a cell.

The excitation light source 11 employed in the apparatus of FIG. 1 may be pulsed and the detector may be fitted with a gating device, so that the time taken for a fluorescent label to emit light following the pulse may be used to distinguish between different labels in a technique termed fluorescent lifetime imaging (FLIM) [ref. R. Cubedda, J. Phys. D: Appl. Phys., 2002, Vol. 35, R61-R76].

An activating light beam 54 may enable a deeper understanding of the dynamic processes in a sample such as a living cell (in many cases this may be based on the excitation light source) to be obtained. The activating light beam may be directed to portions of the sample in such a manner that the intense light from this beam alters the sample and/or bleaches labels present in the sample and reduces their fluorescence. By observing the subsequent changes in the light emanating from this region, and/or elsewhere in the sample, information can be obtained on mechanisms of interaction and/or exchange of various labelled components.

The beam may act to perforate a cell wall to allow the entry of an external agent, to dissect all or part of the cell, to destroy all or part of the cell, or to change the environment of the sample.

Figure 1D:
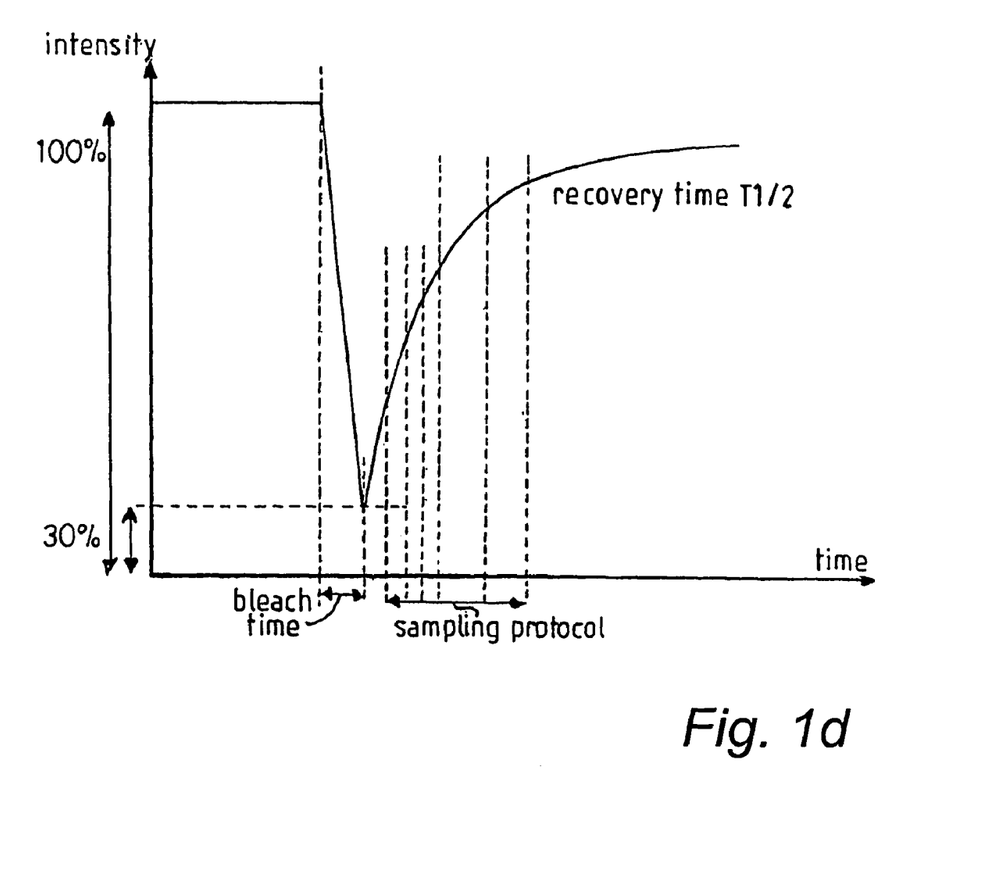
FIG. 1d shows a typical bleach recovery curve for a fluorescent label.

A graph plotting the intensity of fluorescence at a bleached region against time is shown in FIG. 1d.

For example, the rapid recovery of fluorescence at the bleached portion suggests to what extent the label is free to return to the region. The mechanism, diffusion or local synthesis, may be determined by estimation of diffusion rates and the mobile fraction [ref. AxelRod, Biophys. J., 1977, Vol. 18, pp. 129-131.].

Further analysis and experimentation may provide access to information about molecular binding rates, assembly/disassembly and transport mechanisms [ref. J. Lippincott-Schwartz et al, Nature Supp Imaging in Cell Biol, September 2003, S7-S14.]. Such techniques are popular to explore the dynamics and regulation of processes in cells, for example protein trafficking, lifetime and fate (recycling and breakdown).

Figure 1E:
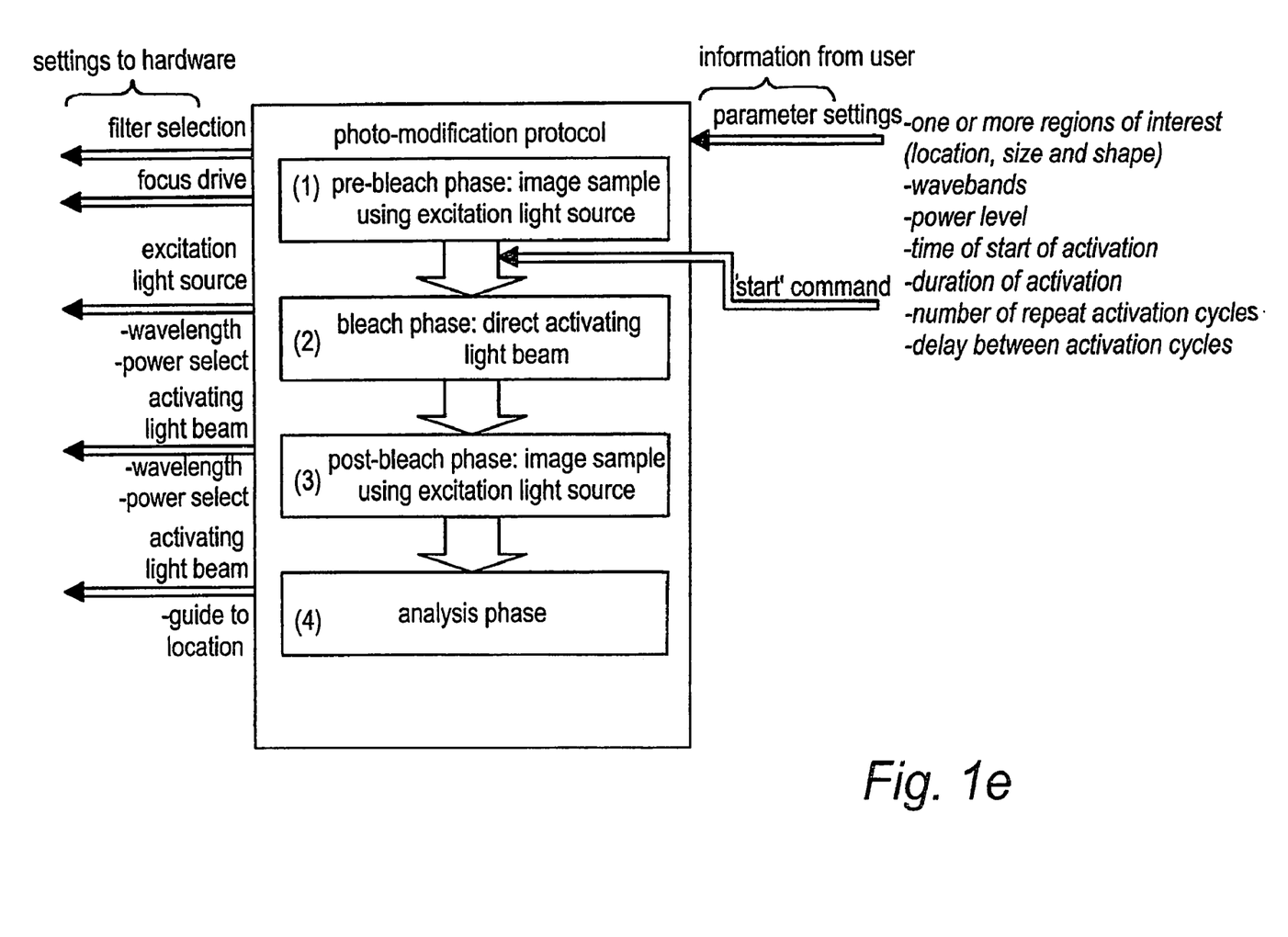
FIG. 1e shows a flow diagram of a known bleaching protocol.

Conventionally, such bleaching techniques may be applied as a "bleaching protocol" comprising four phases as illustrated in FIG. 1e:
(1) a pre-bleach phase in which the sample is imaged using normal fluorescence for a period of time;
(2) a bleach phase during which the activating light beam is directed to illuminate a predefined region with light of a specific wavelength with a specified higher power level for a certain period of time;
(3) a post-bleach phase in which the sample is again imaged using normal fluorescence for a period of time; and
(4) an analysis phase in which the data which has been collected is processed to determine parameters of interest, such as diffusion rate and mobile fraction according to fluorescence intensity in various regions on the image at various time points.

A set of related techniques are commonly referred to as FRAP (Fluorescence recovery after photo-bleaching). Variants of the basic protocol may be used to further explore the system, by repeated bleaching of the same region, and bleaching other portions etc (FLAP, FLIP, iFRAP) [ref. J. Lippincott-Schwartz et al, see above; Phair et al, Nature, 2000, Vol. 404, pp. 604-609.].

Alternatively, a label in the sample, the sample itself or its environment may comprise a caged compound that releases an active group when illuminated by the activating light beam—a process known as uncaging [ref. J. C. Politz, Trend Cell Biol., 1999, Vol. 9, pp. 284-287.]. The active group may be a fluorescent label. Alternatively, the active group may not be a fluorescent label, for example the active group may instead affect the pH of the sample. The active group may have an indirectly visible or otherwise measurable effect on the sample.

In addition a technique known as pattern photo-bleaching may be using to observe changes in structure [ref. J. Ellenberg et al, Nature Supp Imaging in Cell Biol, September 2003, S14-s19.]. In this technique, the bleaching process is used to introduce visually distinctive landmark patterns on part of the sample, for example a grid, movement of which may be tracked over time to understand, for example, mechanisms of membrane deformation or shear.

Recent developments in fluorescent probes has resulted in new labels (photo-switchable labels) which are sensitive to the incident light, in such as way that they change their optical properties, altering their emission spectrum and/or their excitation spectrum. Examples include the photo-activatable GFP (PA-GFP) and Kaede [ref. J. Lippincott-Schwartz et al, see above.]. Furthermore, some of these probes allow their properties to be altered reversibly or irreversibly. Such probes may be activated (made to emit more intensely), or quenched (made to emit less intensely) in different wavebands. For example the kindling FP KFP1 [ref. D. M. Chudakov et al, J. Biol. Chem., 2003, Vol. 278(9), pp. 7215-7219.].

Instrumentation has been developed with an adapted activating light beam to excite photo-switchable labels and force them to undergo the change in optical properties. This may, for example, be useful in revealing or hiding labelled components during the course of an experiment and in studying long term processes such as organism development [ref. D. M. Chudakov et al, Nature Biotechnology, February 2003, Vol. 21, pp. 191-194.].

Hereinafter, the term photo-modification will be used to include photo-bleaching and its variants (FRAP, iFRAP, FLIP, FLAP), photo-activation, photo-switching, and pattern photo-bleaching.

Conventional control of an activating light beam involves setting up a number of activation parameters and requires the user to be able to estimate the appropriate values. In general, these are determined by trial and error using surplus material. It may be desired to set the depth of activation to be say 30% (as is the case in the illustration of FIG. 1d) and the appropriate laser power setting and duration must be determined to achieve this. Similarly, the recovery time of the curve will determine the appropriate sampling regime in the post-bleach period (number of images, interval between images) which in turn is determined by the diffusion coefficient.

These activation parameters must be defined prior to the experiment. They cannot be adapted to suit changing conditions. This means that the approach can only be applied to changing samples by trial and error. Thus fast changes and/or rare events can be extremely difficult to study.

In addition, in existing photo-bleaching procedures, the recovery after bleaching prevents long time course experiments (10 mins+) in the tracking of change since the labels recover over shorter periods and thereafter there is no discernible bleached area.

SUMMARY OF THE INVENTION

The present invention provides a method of analysing a sample of biological material using apparatus including processing means, comprising the steps of:
(a) irradiating the sample with electromagnetic and/or ionizing radiation;
(b) detecting electromagnetic radiation emanating from the sample and generating a signal in response thereto; and
(c) modifying the sample, labels in the sample and/or the environmental conditions of the sample with the apparatus in response to user input after the beginning of step (a) and/or in response to analysis by the processing means of the signal generated in radiation detection step (b).

The present invention may enable combination of imaging, measurement of one or more characteristics in the images collected, and modification of the sample, labels in the sample, and/or the environmental conditions of the sample, with manual and/or automatic determination of the modification parameters according to the measurement made.

In comparison, conventional systems require the user to enter modification parameters manually before the start of the experiment, and so prevent dynamic setting and modification of those parameters, and thus interactive probing of complex systems.

Thus, in accordance with the invention, such modifications may be determined and executed "in real time", interactively, as the experiment progresses. This flexibility allows longer time course experiments to be conducted. It also allows rare, brief and/or rapid events to be detected and acted upon, such as all fertilisation or mutation events. Events that are difficult for a human operator to detect, such as coincident events can be detected and acted upon.

Where the present method is carried out using a light microscope, the irradiation is provided by an illumination light source. The electromagnetic radiation emanating from the sample may in that case be in the form of light transmitted by the sample if illuminated from below, or reflected light if the same is illuminated from above.

In a preferred approach, the sample includes fluorescent labels, step (a) comprises irradiating the sample with excitation energy, and step (b) comprises detecting fluorescent radiation emitted by labels in the sample when excited by the excitation energy.

The excitation energy may be in the form of electromagnetic energy (preferably light) or ionizing radiation, for example.

The modification step (c) may comprise irradiating at least a portion of the sample with an energy beam. If labels are present in the sample, this beam may be selected such that the fluorescence of labels in the portion is reduced or "bleached". In a particular embodiment, steps (a) to (c) are repeated after step (c), the period of time between the end of step (c) and the start of step (a) and/or the parameters of step (c) when repeated being dependent on said analysis by the processing means.

In a preferred embodiment, the apparatus operates so as to cycle between irradiation and modification phases, and the resultant change in the appearance of the sample is detected.

In another approach, the modification step (c) comprises irradiating at least a portion of the sample with an energy beam so as to modify the optical properties of photo-switchable fluorescent labels in the portion.

For example, it may be desirable to measure intra-cell diffusion many times over an extended period. Repeating a known FRAP experiment would have a cumulative photobleaching effect; soon the cell would not be visible. Using photo-switchable labels, a region can be switched rather than bleached. According to the present invention, a diffusion (or other) process may be measured, and when it is determined by the processing means that the process and/or its measurement is complete, the photo-switchable labels may be "quenched", returning them to their original state, before repeating the process. By avoiding repeated photo-bleaching a sample can be imaged for longer, and the present invention enables a process to be repeated and/or a series of measurements to be carried out in response to detected fluorescent radiation over a prolonged period.

Avoidance of repeated photo-bleaching is also beneficial as an activating light beam is often intense and its use may result in damage to the sample, or the creation of reactive species such a singlet oxygen, which may perturb the process under study, requiring sophisticated control experiments, and is thus not truly non-invasive. [Ref. D E Wolf, M Edidin, P R Dragsten, 1980, and Proc. Natl. Acad. Sci. USA 77: 2043-2045.]

After step (c), the environmental conditions of the sample may again be changed and the light emanating from the sample thereafter detected for analysis.

In another embodiment, the environmental change is selected to cause labels in the sample to release a substance.

In a further embodiment, the environmental change is selected to modify the manner in which the sample and/or labels in the sample respond to irradiation. For example, it may change the colour of the sample or the excitation spectrum and/or emission spectrum of labels in the sample. In particular the environmental change may be controlled activation light.

The ability to modify the response of the labels in the course of a process may avoid a need to physically introduce labels during the experiment. The procedures for introducing the labels into the sample during an experiment are quite difficult to master, requiring additional equipment, knowledge and skill on the part of the user. Experiments often have to be repeated many times. In the case of microinjection, such procedures are also invasive to the sample. It can be seen that interactive modification of labels already present in the sample may not require physical introduction of additional labels. Labels may be activated or "switched on" in a selected region.

In a further preferred approach, the modification step (c) comprises modifying the physical structure of at least part of the sample. For example, this may involve forming an opening in a membrane of a selected cell in the sample to allow material to pass therethrough. The opening may be formed using a localised energy beam such as a laser, for example. In this way, an individual cell may be selected in the sample which is exhibiting behaviour of interest, and the user can form an opening in the cell wall to allow material in response to that behaviour. The intensity of the energy beam is preferably selected such that the cell membrane is able to close or "heal" the opening shortly after its formation. Forming an opening in a cell in this way to allow the ingress of genetic material is often referred to as "transfection".

The opening may allow agents such as labels into the cell to interact with or to highlight a specific structure and/or process in the cell, or otherwise alter its optical properties. It may allow genetic material to pass into the cell. Alternatively, material may be allowed to pass into the cell so as to kill it.

In contrast to dispensing a liquid into a sample to alter the composition of the sample as a whole, modification of an individual structure such as a cell is permitted using the technique described above. It may also be employed in combination with liquid dispensing, whereby the liquid dispensing step provides the material which passes through the opening formed by the energy beam.

The environmental conditions of the sample to be changed may be its temperature, the concentration of a certain ion, the pH of the sample, the voltage potential of the sample, the presence of a specific enzyme, or the pressure of the sample. Labels in the sample may be sensitive to these conditions and activate when a predetermined range is reached.

In another embodiment, the environment of the sample is changed by altering the composition of the gas adjacent to the sample. For example, labels in the sample may be activated by exposure to a predetermined gas or concentration of a predetermined gas, such as oxygen.

In a further embodiment, the environment of the sample is changed by irradiating it with activation energy.

The sample may be irradiated with an activation energy beam arranged to irradiate a selected portion of the sample. The beam may define a pattern, such as a grid, for example.

A parameter (or parameters) of the activation energy irradiation determined by the processor may be one or more of the following examples: the start time of the irradiation; the portion of the sample to be irradiated; the waveband(s) of the energy; the power level; the duration of the irradiation; the number of repeat cycles of the activation irradiation energy; and the delay between repeat cycles.

The modification carried out in step (c) of a process embodying the invention may be applied to a region of the sample selected in response to the user input and/or the analysis by the processing means.

A parameter of the modification of step (c) may be determined by the processing means with reference to data stored by the apparatus.

In a further implementation, the modification of step (c) is dependent on detection of the occurrence of a predetermined event in the sample by the processing means.

Preferably, data generated by the analysis by the processing means is stored by the apparatus so as to facilitate reference thereto in determining a parameter of a subsequent modification step.

The invention further provides apparatus for analysing a sample of biological material including fluorescent labels, comprising:

irradiation means for irradiating the sample with electromagnetic and/or ionizing radiation;
   detection means for detecting radiation emanating from the sample and outputting an output signal in response thereto;
   modification means for modifying the sample, labels in the sample, and/or the environmental conditions of the sample;
   processing means for analysing the output signal from the detection means; and
   control means for controlling the modification means in response to user input after irradiation of the sample and/or in response to analysis by the processing means of the output signal from the detection means.

In a preferred embodiment, the apparatus includes data storage means for storing data generated by analysis by the processing means for reference thereto by the control means in determining a parameter of a modification by the modification means.

The apparatus may further include display means for presenting to a user an indication of the electromagnetic radiation detected by the detection means, and input means for enabling a user to control at least one parameter of a modification by the modification means in response to detected radiation. Preferably, the input means enable a user to identify a specific location in a sample for a modification by the modification means.

DETAILED DESCRIPTION OF THE INVENTION

Prior art and embodiments of the invention will now be described by way of example with reference to the accompanying schematic drawings, wherein.

The embodiments described with reference to FIGS. 2 to 7 concern photo-modification of a sample and/or labels in a sample. It will be appreciated that the modification carried out in accordance with the invention may take other forms.

FIGS. 2 to 7 represent diagrammatically protocols followed by processing means of a suitable apparatus, together with associated inputs and control outputs fed to other parts of the apparatus.

Figure 2:
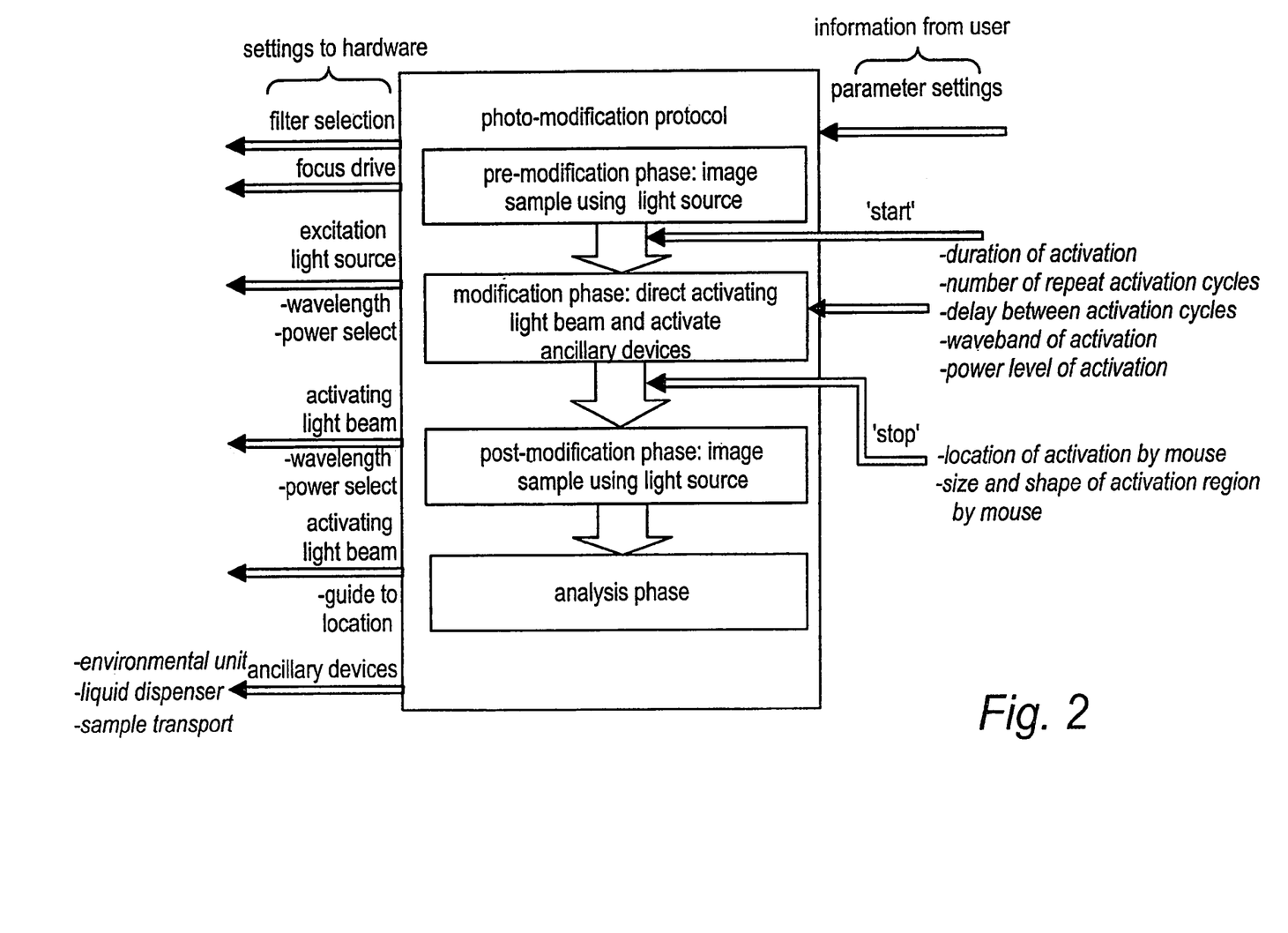
FIGS. 2 to 7 show flow diagrams of modification protocols according to respective embodiments of the invention.

FIG. 2 shows a first embodiment of the invention, which allows interactive control of photo-modification. A user interface allows parameters to be set and/or modified during the running of the experiment. The parameters control operation of the activating light source and/or ancillary devices such as the examples given in the Figure which may modify the sample, labels in the sample and/or the immediate environment of the sample.

In an implementation in which the activating light beam bleaches fluorescent labels in the sample, this protocol may be termed "FRAP on demand".

In the embodiment of FIG. 2, the system allows the user to set the parameters of the activating light beam comprising, the region of interest on the sample, the waveband(s), the power level at those wavebands, and the duration of activation. The user is able to image the sample and determine the start time of activation by a suitable action such as a key press.

The user may be able to determine one or more of the duration or end of activation, the number of repeat cycles and the delay between cycles of activation, and the wavelength of the activation by a suitable action such as a key press.

Furthermore, the user may be able to determine the location of activation and/or the size and shape of the irradiated region by suitable action such as manipulation of an input device such as a computer mouse.

A label may have a temperature sensitive domain, and the sample may be held on a holder, the temperature of which may be controlled by the user via the computer to activate the labels at an appropriate point in a process.

A label may be sensitive to gas such as oxygen, and the sample environmental unit controlled by the user via the computer to activate the labels in the course of an experiment.

Figure 3:
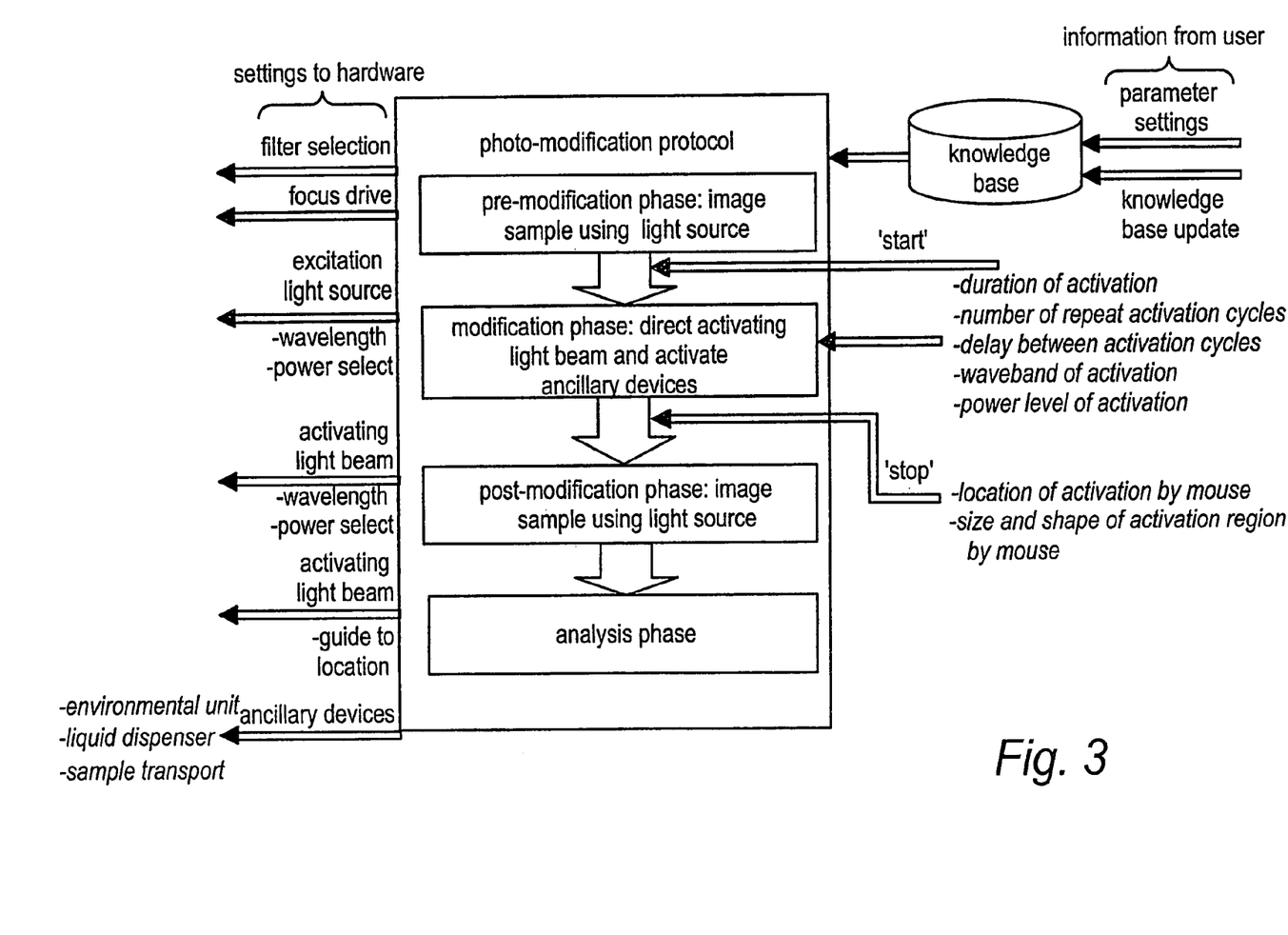

FIG. 3 shows a second embodiment that allows the use of a knowledge base to assist the user in setting and/or modifying the parameters.

In the embodiment of FIG. 3, the system is as FIG. 2, and additionally allows a less experienced user to set certain high level parameters of photo-modification parameters such as the type of label to be bleached, and the system uses a knowledge base to determine the low level parameters to be used by the hardware, such as the wavelength and power level.

Additionally, a more experienced user may be able to modify the knowledge base.

In an implementation in which the activating light beam bleaches fluorescent labels in the sample, this protocol may be termed "expert FRAP".

Figure 4A:
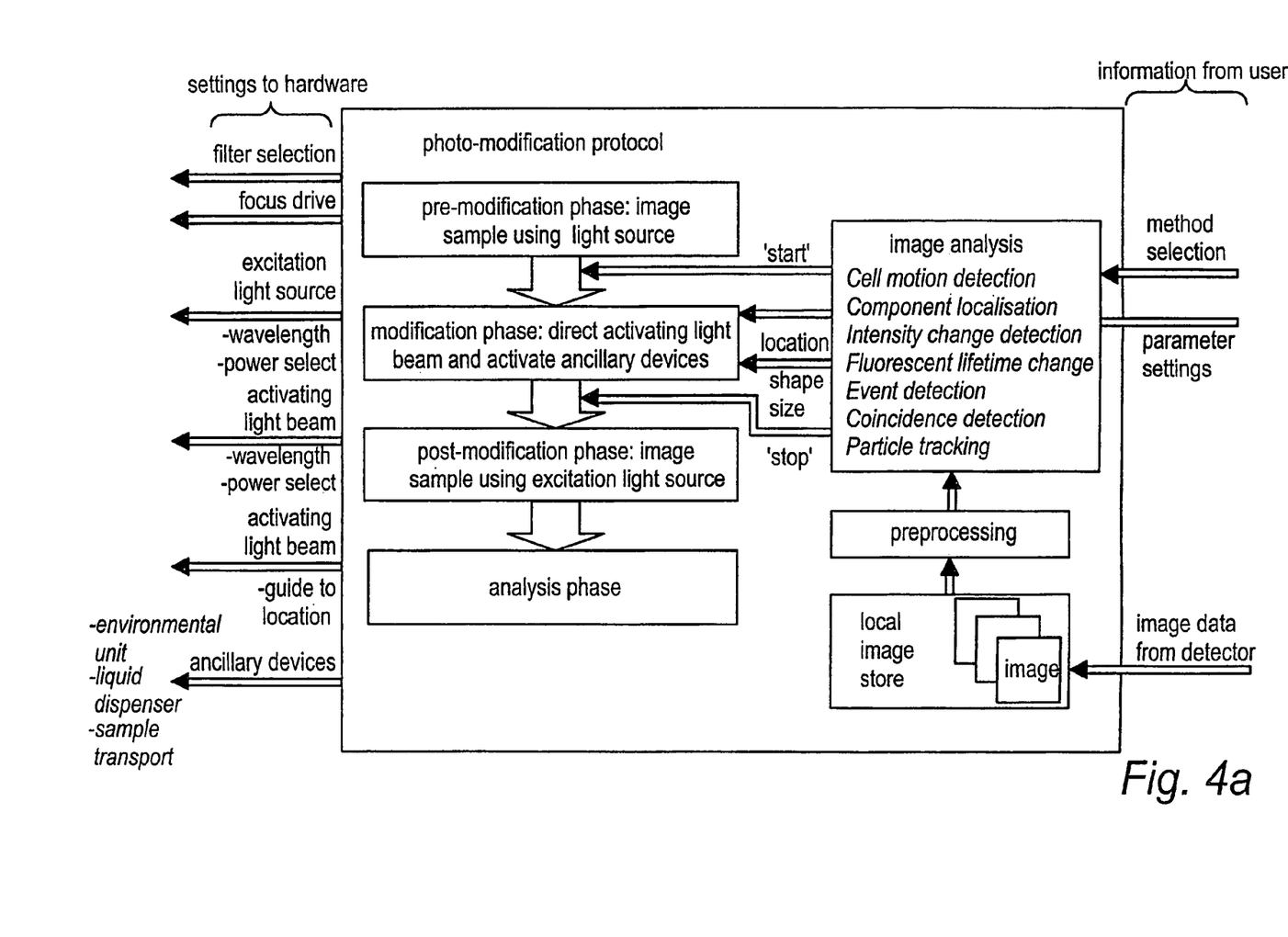

FIG. 4a shows a third embodiment that uses information extracted from the images collected during the pre-modification (observation) phase to set the photo-modification parameters.

In an implementation in which the activating light beam bleaches fluorescent labels in the sample, this protocol may be termed "clever FRAP".

Figure 4B:
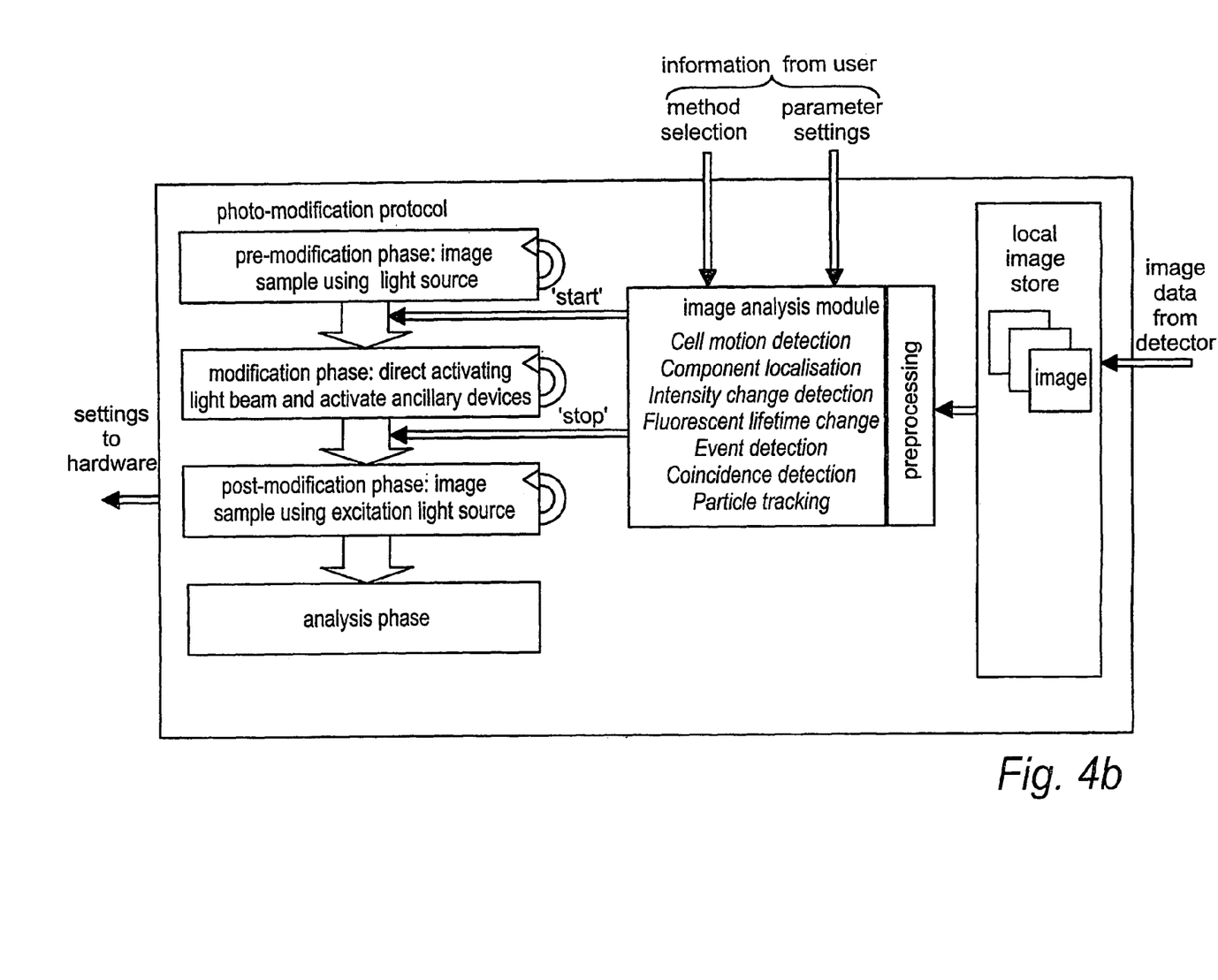

FIG. 4b shows the third embodiment implemented in the form of a state machine. Each phase in the protocol is repeated until an exit condition is met. For the pre-modification phase, the exit condition is when the image analysis module sends the start signal. For the modification phase, the exit condition is when the image analysis module sends the stop signal. The additional parameters to send are not shown in this diagram.

In the embodiment of FIGS. 4a and 4b, the system allows the user to set certain parameters of the activating light beam, whilst setting others on the basis of information extracted from the data acquired during the pre-modification phase. In particular, the image data may be analysed to detect an event such as the motion of a component in the sample such as a cell in order to trigger the activating light beam.

The user may be able to determine the duration or end of activation by suitable action such as a key press.

The data may be analysed to:
  determine location of a moving portion of the sample to direct the activating light beam;
  determine a change in intensity of part of the sample to direct the activating light beam;
  determine relative change in intensity of part of the sample to direct the activating light beam;
  determine relative change in fluorescent lifetime of part of the sample to direct the activating light beam;
  locate one or more substructures of interest, such as cellular components, organelles, vesicles or other particles, where the location and/or size of the particle(s) is used to direct the activating light beam;
  locate one or more substructures of interest such as cellular components, organelles, vesicles or other particles, where the location, motion, shape, speed, direction, relative distance and/or size of the particle(s) is used to trigger the activating light beam;
  detect key events in the cell cycle (such as cell division, cell death, viral invasion, endoctyosis, exocytosis, tubulation, gene transfer etc.) and/or coincidence of more than one event to trigger the activating light beam;
  automatically control the instrument;
  direct the setting of the irradiation source;
  direct the setting of the emission wavelength. For example, by following changes in emission wavelength and adjusting the wavelength of the irradiation light to maximise the emission intensity of labels in a sample, it is possible to measure changes to characteristics of the sample and do so more effectively;
  direct the setting of the polarisation of the light;
  direct the setting of the focus drive mechanism and thus the plane of focus of the microscope;
  direct a sample transport mechanism;
  set the temperature of a sample heater; and
  control a liquid dispensing mechanism.

The data may be preprocessed to remove distortions due to deformation or motion of all or part of the sample.

Figure 5:
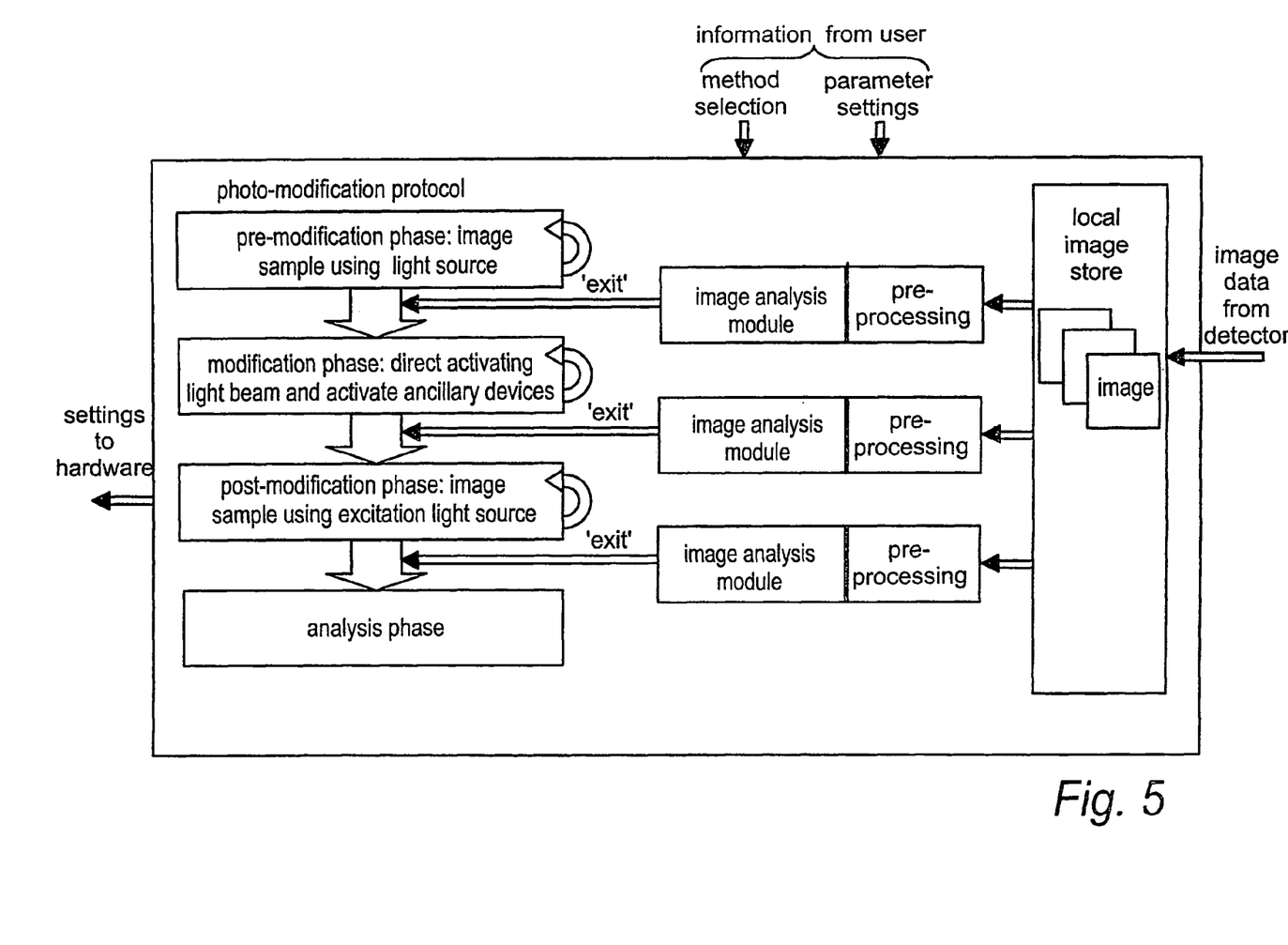

FIG. 5 shows a fourth embodiment in which an image analysis module processes the image data acquired at each phase to determine the most appropriate parameter settings, for example, the amount of light to in order to complete photo-modification.

In the embodiment of FIG. 5, the system allows the user to set certain parameters of the activating light beam, whilst the system sets others on the basis of information extracted from the data acquired during the pre-bleach phase, during the bleach phase, and during the post-bleach phase. In particular, the image data may be analysed to detect an event such as the change of a component in the sample in order to end a phase.

Figure 6:
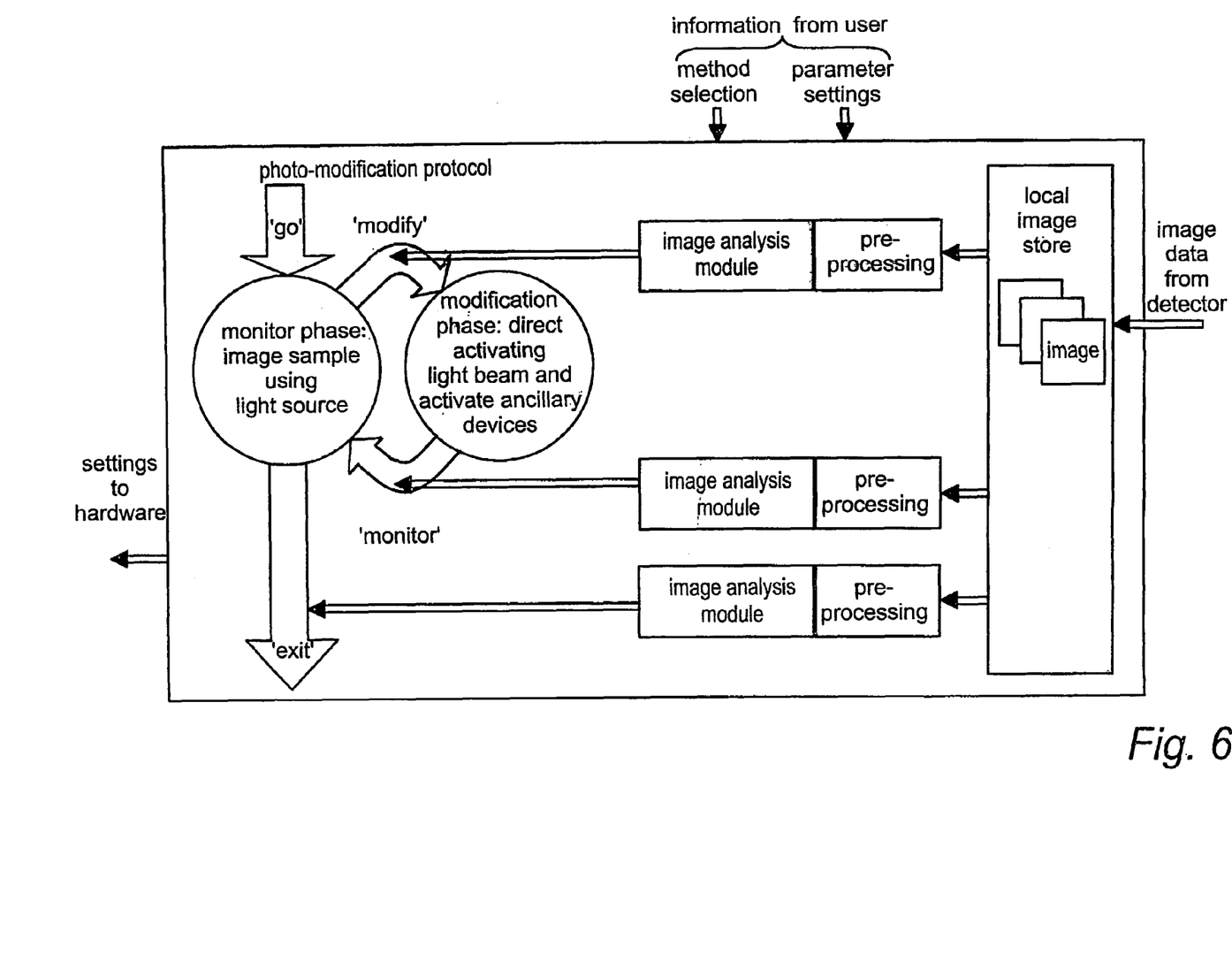

FIG. 6 shows a fifth embodiment in which the system moves from a monitor phase to a modification phase according to the information extracted from the images collected. In an implementation in which the activating light beam bleaches fluorescent labels in the sample, this protocol may be termed "automated FRAP".

This is expected to be particularly useful when used in conjunction with photo-switching labels which can be activated and quenched repeatedly and used to track the lifecycle of individual components.

In the embodiment of FIG. 6, the system allows the switching between a monitor phase during which the sample is imaged using the excitation light source, and a modification phase, during which the sample is imaged using the activating light source. The transition between the two phases and parameters for the phase is determined by the analysis of the image data collected.

Figure 7:
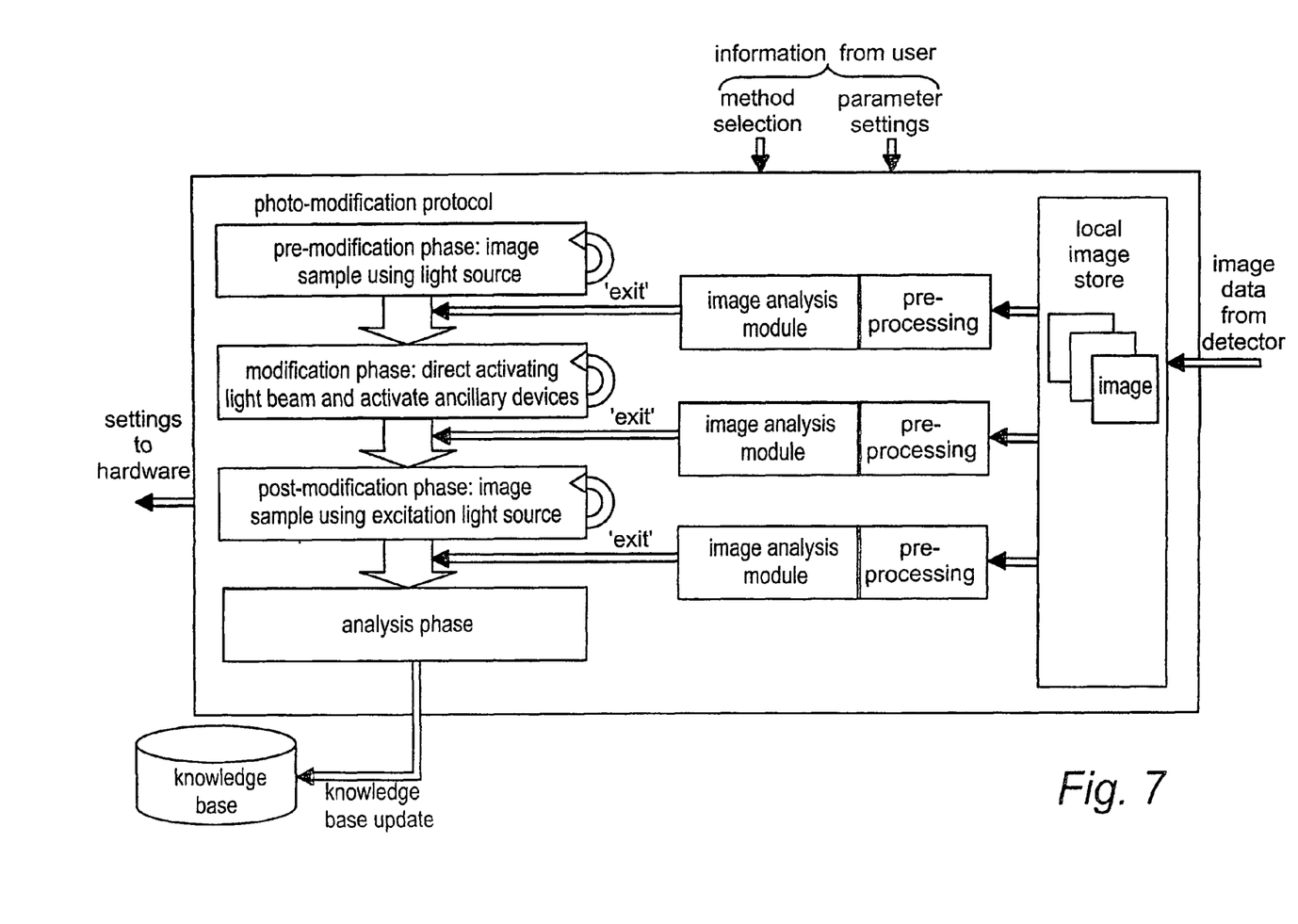

FIG. 7 shows a sixth embodiment in which the system moves from a monitor phase to a modification phase according to the information extracted from the images acquired and collects the information about the sample behaviour to the activating beam at a number of parameter settings so as to set up the knowledge base mentioned in FIG. 3. In an implementation in which the activating light beam bleaches fluorescent labels in the sample, this protocol may be termed "autoconfig FRAP".

In the embodiment of FIG. 7, the system allows the control of the pre-modification phase, modification phase, post-modification phase and analysis phase as described in relation to FIG. 5. The parameters used at each stage are those that permit an exploration of the possible parameters of the sample so as to quickly and efficiently determine the hardware settings (laser power, modification duration, etc) by an iterative process, and these settings are passed to knowledge base mentioned in connection with FIG. 3. With the appropriate filter sets, the system may be able to image during the modification phase, for example during a bleach process, to monitor the parameters of the modification.

In a further embodiment, the sample contains one or more photo-switchable labels, so that the activating light beam is able to activate, quench or switch the label as described above in order to observe the labelled component over short (fast moving components), medium, or long time scales (rare events or configurations).

The labels may comprise a naturally occurring fluorescent molecule such as NADH, a calcium probe such as "Fura", and/or an antibody tagged with a fluorescent molecule and bound to a selected species.

The labels may comprise a pair of fluorescent molecules with overlapping emission-excitation spectra of the types used in fluorescence resonant energy transfer ("FRET"), and the activating light beam may be set to photo-bleach the acceptor molecule in a region of the sample, so that the FRET process may be confirmed in that region.

One of the FRET pair may be a photo-switching label, and the activating light beam may be set to switch the photo-switching label in a region of the sample, so that the FRETing process may be confirmed in that region.

The labels may comprise a caged compound that releases an active group when illuminated by the activating light beam [ref. J. C. Politz, see above.].

In a further embodiment, the excitation light source 11 may emit one or more spectral bands from a broadband light source such as a lamp. Furthermore, the excitation light source may be controllable to provide excitation light at more than one distinct waveband in order to distinguish between different labels. In some processes, it may be advantageous for the excitation light source to be pulsed.

The excitation light source may be of the type employed in fluorescent speckle microscopy [ref. M. C. Adams et al, Methods, 2002, Vol. 29, pp. 29-41.]).

In a further embodiment, the activating light beam may be derived from the same source as the excitation light.

The activating light beam may be:
pulsed;
an optical trap or optical tweezer arrangement;
a laser dissection mechanism for removing a region of interest from the sample for subsequent handling; or
a laser ablation mechanism for removing a region of interest from the sample for subsequent handling.

A localised energy beam may be employed to form an opening in a structure, such as a cell, in response to detected radiation emanating from a sample. Preferably, a laser is used. This may be a Ti:sapphire, argon-ion or frequency-shifted Nd:YAG laser for example. Alternatively, a diode laser can be employed which may be less costly.

Exposing a cell to 0.3 mW of violet light from a diode laser for 40 ms has been found to perforate a cell membrane. The beam was focussed onto the cell using a ×100 microscope objective lens to form a spot about 1 micron in diameter. This results in a power density of around 1200 MW/m$^2$. The cell membrane was able to "heal" itself shortly after the process without apparently suffering any long term damage or mutation [ref. Optics Express, Vol. 13, page 595].

The same light source may be used to generate the localised energy beam to form an opening in a structure as is used to generate the activating light beam, and for the excitation light beam.

In a further embodiment, the system may have one or more photo-detectors such as photo-multiplier tubes and a scanning arrangement of the excitation light beam and/or the emission light path to the detector and/or the detector to observe parts or all the sample.

The system may have more than one imaging detector fitted with different light filtering components to distinguish between different labels.

The detector may be fitted with a gating device, and the excitation light source may be pulsed, so that the time taken for the fluorescent label to emit light following the pulse may be used to distinguish between different labels.

The controller may be implemented in hardware and/or software.

In a further embodiment, the system may use a confocal principle, collecting light at a single image plane by the use of one or more pinholes and a scanning mechanism.

Alternatively, a structured illumination technique may be utilised to section a sample optically at different depths [ref. M. A. A. Neil, R. Juskaitis and T. Wilson, Optical Letters, 22(24): 1905-1907, Dec. 15 1997]. This may be more cost effective than a laser scanning confocal system, as it can be carried out using a conventional light microscope.

A total internal reflection (TIRF) principle may be employed in which the excitation light source is directed to be internally reflected at the sample-sample carrier surface, thus exciting only parts of the sample close to the surface [ref. Y. Sako and T. Yanagida, Nature Supp Imaging in Cell Biol, September 2003, SS1-SS5.].

Furthermore, the system may use a deconvolution principle, capturing a group of images focused at different imaging planes, and applying a deconvolution process to allow volumetric (XYZ) data to be acquired. Volumetric time series (XYZT) data, volumetric multi-wavelength (XYWZ) data, or volumetric multi-wavelength time series (XYWZT) data may be acquired.

A multi-photon microscope employing a long wavelength (800-1200 nm) high speed pulsed laser may form the excitation light source and/or as the activating light beam [ref. J. Pawley, Handbook of Confocal Microscopy].

The light or fluorescence microscope may be replaced with a simplified arrangement of sample holder, magnifying objective lens and dichroic mirror to direct light from the irradiation light source and the activating light beam to the sample, and collect the emitted light beam and to direct it to a detector.

Alternatively, the fluorescence microscope may be replaced by an endoscope.

The sample may be a homogenous population of cells such as a cell culture. Alternatively, the sample may be a heterogenous multi-cellular assembly such as a cell culture; a multi-cellular assembly such as a tissue culture; a stem cell sample; a tissue sample; an organ, such as an eye or retina, or the inside of the gut or a blood vessel; a whole animal, such as the worm *C. elegans*, an insect, fish, mammal or amphibian; a whole or part of a plant or fungus, a dividing cell or an embryo; one or more samples held in a multi-site carrier such as a slide, or a multi-well plate, which is scanned sequentially; or a material sample undergoing some change such as diffusion of one or more species.

The invention claimed is:

1. A method of analyzing a sample of biological material including fluorescent labels using apparatus including a processing arrangement, comprising the steps of:
   (a) irradiating the sample with excitation energy;
   (b) detecting fluorescent radiation emitted by labels in the sample when excited by the excitation energy;
   (c) creating images of the sample according to the light detected in step (b);
   (d) analyzing said images to detect the occurrence of a predetermined event in the sample; and
   (e) modifying at least one of: (i) the sample by irradiating a selected portion of the sample with an energy beam, (ii) labels in the sample by irradiating a selected portion of the sample with an energy beam, and (iii) the environmental conditions of the sample with the apparatus, in response to detection of said predetermined event in analysis step (d) either by a user providing user input or by the processing arrangement.

2. A method of claim 1 wherein the modification step (e) comprises irradiating a selected portion of the sample with an energy beam such that the fluorescence of labels in the portion is reduced.

3. A method of claim 2 wherein steps (a) to (e) are repeated after step (e), the period of time between the end of step (e) and the start of step (a) and/or the parameters of step (e) when repeated being dependent on analysis step (d).

4. A method of claim 3 comprising forming an opening in a membrane of a selected cell in the sample to allow material to pass through the opening into the cell.

5. A method of claim 4 wherein the opening is formed using a localized energy beam.

6. A method of claim 1 wherein the modification step (e) comprises irradiating at least a portion of the sample with an energy beam so as to modify the optical properties of photoswitchable fluorescent labels in the portion.

7. A method of claim 1 wherein the modification step (e) comprises modifying the physical structure of at least part of the sample.

8. A method of claim 1 wherein the modification of step (e) is applied to a region of the sample selected in response to the user input and/or the analysis by the processing arrangement.

9. A method of claim 1 wherein the at least one parameter of the modification of step (e) is determined by the processing arrangement with reference to data stored by the apparatus.

10. A method of claim 1 wherein data generated by the analysis by the processing arrangement is stored by the apparatus so as to facilitate reference thereto in determining a parameter of a subsequent modification step.

11. Apparatus for analyzing a sample of biological material including fluorescent labels, comprising:

an irradiation arrangement for irradiating the sample with excitation energy;

a detection arrangement for detecting fluorescence radiation emitted by labels in the sample when excited by the excitation energy and outputting an output signal in response thereto;

a processing arrangement for processing the output signal from the detection arrangement to create images of the sample;

a modification arrangement for modifying at least one of the sample and labels in the sample and the environmental conditions of the sample; and a control arrangement for controlling the modification arrangement so as to irradiate a selected portion of the sample with an energy beam and/or to modify the environmental conditions of the sample in response to detection of the occurrence of a predetermined event in the sample by analysis of said images either by a user providing user input or by the processing arrangement.

12. Apparatus of claim 11 including a data storage arrangement for storing data generated by analysis by the processing arrangement for reference thereto by the control arrangement in determining a parameter of a modification by the modification arrangement.

13. Apparatus of claim 11 including a display arrangement for presenting to a user an indication of the fluorescent radiation detected by the detection arrangement, and an input arrangement for enabling a user to control at least one parameter of a modification by the modification arrangement in response to detected fluorescent radiation.

14. Apparatus of claim 13 wherein the input arrangement enables a user to identify a specific location in a sample for a modification by the modification arrangement.

\* \* \* \* \*